United States Patent [19]

Lin et al.

[11] Patent Number: 4,994,593
[45] Date of Patent: Feb. 19, 1991

[54] HYDROXYLHYDROCARBYL-MODIFIED AMINOALKYL SILICONES

[75] Inventors: Samuel Lin, Paramus, N.J.; Colleen Parriott, Monroe, N.Y.

[73] Assignee: Chesebrough-Pond's USA Co. Division of Conopco, Inc., Greenwich, Conn.

[21] Appl. No.: 449,360

[22] Filed: Dec. 6, 1989

Related U.S. Application Data

[63] Continuation of Ser. No. 276,726, Nov. 28, 1988, abandoned.

[51] Int. Cl.$^5$ .............................................. C07F 7/10
[52] U.S. Cl. ................................................... 556/424
[58] Field of Search ........................................ 556/424

[56] References Cited

U.S. PATENT DOCUMENTS

| | | | |
|---|---|---|---|
| 2,806,814 | 9/1957 | Richter | 167/93 |
| 3,032,577 | 5/1962 | Morehouse | 556/424 X |
| 3,152,161 | 10/1964 | Sisauke et al. | 556/424 |
| 3,402,191 | 9/1968 | Morehouse | 556/413 |
| 3,624,120 | 12/1971 | Yetter | 556/413 |
| 3,860,709 | 1/1975 | Abbott et al. | 424/184 |
| 4,450,152 | 5/1984 | Ona et al. | 424/70 |
| 4,485,090 | 11/1984 | Chang | 424/52 |
| 4,507,455 | 3/1985 | Tangney et al. | 528/26 |
| 4,510,127 | 4/1985 | Chang | 424/52 |

FOREIGN PATENT DOCUMENTS

| | | | |
|---|---|---|---|
| 3705121 | 9/1988 | Fed. Rep. of Germany | 556/424 |
| 1447254 | 8/1976 | United Kingdom | 556/413 |

*Primary Examiner*—Paul F. Shaver
*Attorney, Agent, or Firm*—Gerard J. McGowan, Jr.

[57] ABSTRACT

Amino alkyl silicones modified by reaction with epoxide groups, thereby alkylating the amines. The alkylated amines show decreased reactivity toward aldehydes which may be present in consumr products. The modified amino alkyl silicones may be used in dentifrices and other consumer products.

23 Claims, No Drawings

HYDROXYLHYDROCARBYL-MODIFIED AMINOALKYL SILICONES

This is a continuation of Ser. No. 276,726, filed Nov. 28, 1988, abandoned.

FIELD OF THE INVENTION

The application concerns novel aminoalkylsilicone compounds which are useful in dentifrices and other consumer products.

BACKGROUND OF THE INVENTION

Great strides have been made in recent years in the field of oral health care. However, much remains to be done. While the development of anticaries agents, especially the fluorides, has led to a decline in the incidence of tooth caries it is desirable to even further decrease the number of teeth affected thereby. Moreover, attention in the oral health care field has increasingly focused on the problems of gum disease, periodontitis. While antibacterial agents have been proposed of inclusion in products for use by consumers in the treatment of periodontitis, certain problems have been associated with their use. For example, use of chlorhexidine, which has been known as as antibacterial agent, has been associated with staining problems; it produces yellow to dark brown stains on teeth, tongue and oral mucosa. Furthermore, chlorhexidine has a very bitter taste.

There has been a need, therefore, for developing a dentifrice formulation including chlorhexidine or other antimicrobial agents such as quaternary ammonium antibacterial compounds, which does not cause staining of the teeth and which has an improved taste. Moreover, dentifrices having improved anticavity effects are also desirable.

Staining can be troublesome, whether or not chlorhexidine is the cause. The accumulation of stains on tooth surfaces poses an esthetic problem for many individuals.

Plaque is a common factor in caries, gum disease and staining and greatly contributes to their development. Proper oral hygiene as currently practiced requires that plaque be removed or prevented not only for cosmetic purposes but also to eliminate a source of potential injury to teeth and gums.

Silicones have previously been suggested for inclusion in dentifrice compositions in that it has been proposed that they would coat the teeth and thereby prevent cavities and staining. For example, British Patent Specification 689,679 discloses a mouthwash containing an organopolysiloxane for the purpose of preventing adhesion of, or for removal of, tars, stains, tartar and food particles from the teeth. However, polymers such as those disclosed in the '679 specification, have not generally been successfully used for coating the teeth since it has been found that the polysiloxane does not adhere to the teeth for prolonged periods of time. Therefore, the need for dentifrice formulations including a hydrophobic substance which effectively coats the teeth has not been satisfied.

Viccaro, et al. copending application S/N 07/276,704 field Nov. 28, 1988 and entitled "Dentifrices Containing Aminoalkyl Silicones" discloses dentifrice formulations including aminoalkylsilicones for coating the teeth and inhibiting stain and caries. The aminoalkylsilicones have been found to be more substantive than alkylsilicones, apparently due to the interaction of the positively charged nitrogen of the amine with the negative charges on the surface of the teeth. However, amine groups tend to react with certain chemical groups found in toothpaste components such as the aldehydes of flavoring ingredients. Consequently, aminoalkylsilicones bearing amine groups capable of being protonated over a broad pH range yet of reduced reactivity are desirable.

Silicones have been used or proposed for use in many consumer products other than dentifrices. Where silicones are included to coat charged objects, such as furs, aminoalkylsilicones will be of use. Like dentifrices, these products may contain compounds having moieties which tend to react undesirably with amine groups. Therefore, aminoalkylsilicones in which the amine group is somewhat deactivated would be useful in these applications, as well.

Attempts have been made to modify the structure of aminosilicones to decrease the reactivity of the amino groups. In U.S. Pat. No. 4,507,455 aminosilicones are reacted with acetic anhydride to form amides. It is believed that the modifications seriously limit the pH range over which the amines will be protonated thereby detracting from the usefulness of the respective aminoalkylsilicones in applications, such as those mentioned above, wherein protonation of the amine is important. Also, U.S. Pat. No. 4,472,566 discloses the reaction of aminosilicones with benzylchloride to yield secondary and tertiary amines.

Morehouse U.S. Pat. No. 3,032,577 discloses organosiloxanes which are said to be useful for a variety of applications in the synthetic polymer art, particularly as flocculating agents for aqueous dispersion of clay. The organosiloxanes of the Morehouse patent include units of the formula:

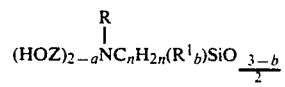

wherein —OZ— is the divalent group derived from a monoepoxide by opening of the oxirane ring, HO is interconnected to N through 2 carbon atoms, a is an integer from 0 to 1, n is an integer from 3 to 15, and R may be hydrogen, monovalent hydrocarbon or —$C_nH_{2n}(R^1b)SiO_{(32-b)}$.; Morehouse does not appear to suggest that his compounds would be useful in dentifrices and the like, nor does he seem to recognize the desirability of using compounds which can yield a higher positive charge density.

SUMMARY OF THE INVENTION

We have now discovered a novel class of modified aminosilicones which have reduced reactivity but still retain positive charges over a broad pH range. The invention also embraces the process of making the components, and compositions employing them. The silicones of this invention are produced by treating silicones containing primary or secondary amine functional groups with epoxides such as ethylene oxide. This reaction effectively converts most amines to tertiary amines with one or two beta-hydroxylhydrocarbyl substituents. The tertiary molecular structure and the electron withdrawing property of beta-hydroxyls reduce the amine reactivity, but still maintain the pKa between seven and nine. Thus, in most formulation conditions, these novel silicones remain as cationic polymers and have good physical interactions with the substrate surface but show reduced chemical reactivities toward flavoring agents, dyes and skin.

The novel silicones of the invention comprise an organosiloxane including at least one unit of formula A:

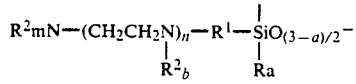
A wherein a is from 0 to 2, n is from 1 to 5, R is a monovalent radical, $R^1$ is a divalent hydrocarbon radical, $R^2$ is

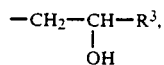

$R^3$ is selected from the group consisting of hydrogen and monovalent hydrocarbon radicals, m is 1 or 2, and b is 0 or 1. One or more nitrogens may also be quaternized; in the case of quaternization of their respective nitrogens, b would equal 2 and m would equal 3.

R is preferably selected from the group consisting of hydrocarbon radicals, halogenated hydrocarbon radicals, hydrogen, hydroxyl, and alkyoxyl groups. Especially preferred are methyl, phenyl and trifluoropropyl. R groups having from 1 to 10 and particularly 1 to 4 carbon atoms are preferred. The divalent hydrocarbon radical of $R^1$ preferably includes from 1 to 20 carbon atoms, preferably 3 to 20 carbon atoms. Preferred $R^3$ groups include hydrogen, hydrocarbon radicals, methyl or phenyl. Hydrogen and methyl are particularly preferred. Where $R^3$ is a hydrocarbon radical, it is preferred that the radical includes 30 or fewer carbon atoms, even more preferably 20 or fewer. Depending on the use to which the compounds are put, it may be desirable that $R^3$ include 10 or fewer, or even 4 or fewer, carbon atoms 4 or fewer. $R_3$ may be saturated, unsaturated, cyclic, acyclic, alkyl or aromatic. n is preferably 1; m is preferably 2; and b is preferably 1.

Examples of the units of formula A are:

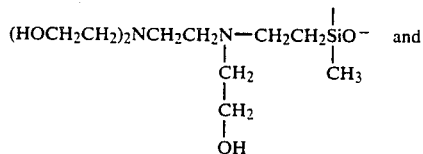

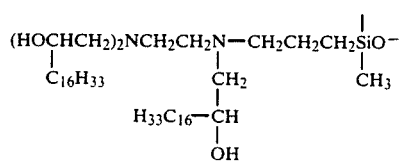

Preferably, the units of Formula A are present in the organosiloxane with units of Formula B:

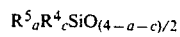
B wherein $R^4$ and $R^5$ are the same or different monovalent radicals, a and c are integers of 0, 1, 2 or 3 and a plus c is 1, 2 or 3. Preferably $R^4$ and $R^5$ are hydrocarbon radicals, halogenated hydrocarbons, hydrogen, hydroxyl or alkoxyl. Methyl, phenyl and -trifluoropropyl are especially preferred for $R^4$ and $R^5$. Generally, $R^4$ and $R^5$ will include from 1 to 20 carbon atoms, preferably from 1 to 10 carbon atoms, more preferably from 1 to 4 carbon atoms. It is particularly preferred that a plus c equal 2.

Preferably, each of the "R" groups described above, e.g., R, $R^1$, $R^2$, etc. includes no greater than 20 carbon atoms, even more preferably no greater than 10 carbon atoms.

The modified aminosilicones of the invention include at least 1 unit of Formula A, and preferably units of Formula B, as well, and may be in the form of random copolymers, block copolymers, linear polymers or branched polymers. The content of Formula A in the polymer ranges by number of repeat units between 0.5% and 100%, preferably between 1% and 10%, more preferably between 5 and 10%. The molecular weight of the modified aminoalkyl silicone preferably ranges from 1000 to 100,000. Molecular weights above 5000 are strongly preferred for a compound which will effectively provide a hydrophobic barrier for a surface. 100,000 is the preferred molecular weight ceiling. A viscosity in the range of 50 cps to 3000 cps is preferred.

Examples of the modified polysiloxanes of the invention are as follows:

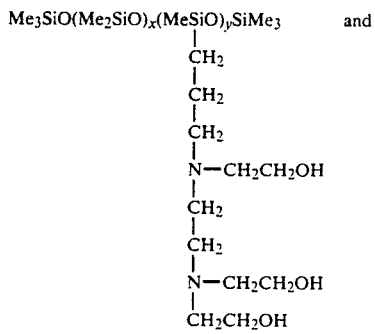

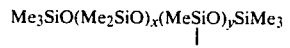

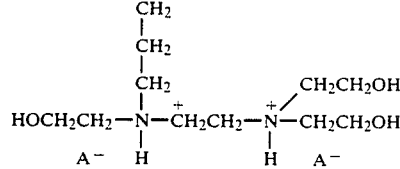

wherein x=1000, y=50 and A— is a counter ion.

DETAILED DESCRIPTION OF THE INVENTION

The compounds of the invention may be prepared by mixing epoxide compounds with aminosilicones in a pressure reactor and heating for about 24 hours, after which the unreacted epoxide compound is vacuum stripped off. The amount of epoxide to be used is calculated based upon the amount of amine functional groups on the aminoalkyl silicone. Preferably, 2 epoxides are reacted for every primary amine and one epoxide for every secondary amine, in order to convert them to tertiary amines. A stoichiometric amount or up to 25% excess of epoxide can be used. The reaction is preferably conducted between 25° C and 150° C, especially between 50° C. and 100° C. The pressure is preferably maintained from 50 psi to 300 psi; particularly from 50 psi to 150 psi. Typical aminosilicone starting compounds would include Dow Corning Q2-8075.

The compounds of the invention are useful in numerous consumer products which employ silicones, including hard surface cleaners, shampoos, waterproofing agents and car waxes.

Dentifrices which include aminoalkyl silicones of the invention can be used to form a hydrophobic barrier on the surface of teeth which is useful in preventing staining of teeth and in preventing cavities. Yet, the modified compounds tend not to react with aldehydic flavors and other amine-reactive compounds. The antistaining properties of dentifrices incorporating the modified aminosilicones of the invention are of particular significance when the compounds of the invention are used in conjunction with a quaternary ammonium salt such as chlorhexidine. In such event, the dentifrice provides the antistain and anticaries benefit of the aminoalkyl silicone together with the antibacterial and gum disease-fighting benefits of the quaternary ammonium salt, without the usual disadvantage of staining. Anti-calculus effects may also result. The antistaining properties of the amino alkyl silicones may likewise be of use when other staining compounds such as stannous fluoride are included in a dentifrice.

It is our view that the positively charged nitrogen-containing silicones of the invention are attracted to negatively charges surfaces such as enamel so that silicones including alkyl amine groups are more substantive to the surface of teeth and other charged surfaces. Moreover, increasing the number of aminoalkyl groups per molecule enhances the substantivity of the silicone. Also, increasing the charge density improves substantivity, as well. At the same time, modification of the aminoalkyl silicones in accordance with the invention decreases the reactivity of the amino groups toward aldehydes and other reactive groups found in some consumer products including dentifrices.

The modified aminoalkyl silicones of the invention may be used in the form of oils or emulsions.

A preferred class of aminoalkyl silicone are the amodimethicones.

Dentifrices including the compounds of the invention are disclosed in greater detail in Lin et al. application S/N 07/276,719 filed Nov. 28, 1988 entitled "Dentifrices Including Modified Aminoalkyl Silicones" and incorporated by reference herein.

The modified amines of the invention become protonated and bear positive charges when the pH is below their pKas. Depending on structure, the pKas will range from about 7 to about 9.5.

The aminoalkyl polysiloxanes which are to be modified in accordance with the invention may be end capped. If end capped, one or more of the end capping groups, $R_e$, preferably includes one or more nitrogen atoms. For example, $R_e$ may be $-(CH_2)_3-NH_2$ or $-(CH_2)_3-NHCH_2CH_2-NH_2$.

As indicated above, a preferred class of aminoalkyl polysiloxanes useful in preparing the compounds of the invention is that of the amodimethicones. Amodimethicones are polydimethyl siloxane polymers containing aminoalkyl groups. The aminoalkyl groups may be present either pendent or at one or more ends of the polydimethylsiloxane chain. The modified amine groups cause the amodimethicone polymer to develop a net positive charge in aqueous systems over a wide range of pH say, from pH 1 to 9. Amodimethicones are commercially available and include Dow Corning Q2-8075 mentioned above.

The following specific examples further illustrate the invention, but the invention is not limited thereto.

ALKYLATION OF AMINE FUNCTIONAL SILANE MONOMER

Example 1

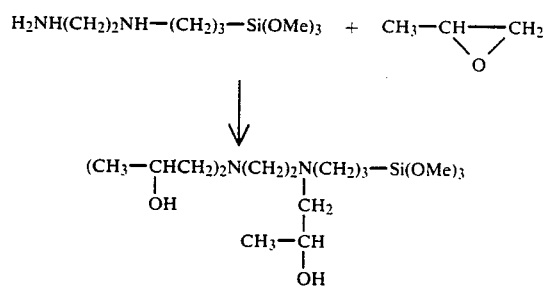

50 g of N—2-aminoethyl—3-amino propyl trimethoxy silane (ex Petrarch), 39.2 g of propylene oxide (ex Aldrich) and 90 g of 2-propanol were reacted together and then stripped of the solvent.

The product was a reactive silicone which precipitated out during the amine titration.

ALKYLATION OF AMINO FUNCTIONAL POLYDIMETHYLSILOXANE COPOLYMER

EXAMPLE 2

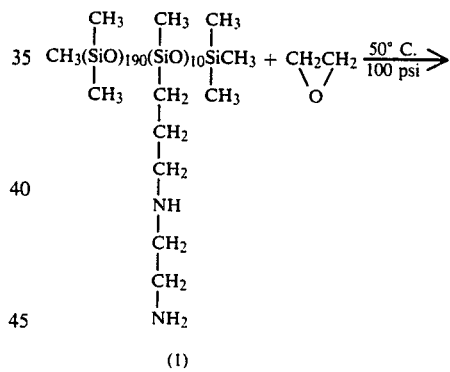

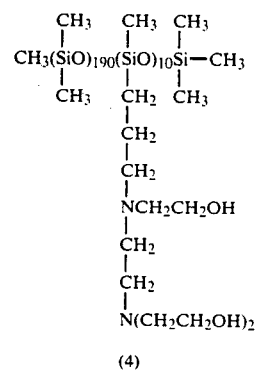

Into a cooled Parr Pressure Reactor was placed 80 g of amodimethicone Oil (1) and 6.5g of ethylene oxide. The contents were then heated at 50° C. and 100 psi and stirred for approximately 24 hours. Within 0.5 hours of the start of the reaction, an exotherm was observed at 75° C. After the 24 hour reaction time, the heat was removed and the contents cooled to room temperature. Following this the pressure was released from the reactor and the unreacted epoxide removed by just bubbling through concentrated sodium hydroxide solution followed by evaporation under reduced pressure.

The product was analyzed for amine content (total, secondary plus tertiary, and tertiary) via potentiometric titration, (see Official and Tentative Methods of the American Oil Chemists Society; Tf 1a-64 and Tf 2a-64). As indicated below, 93% of the amine was present in its tertiary form.

Results of Titration - Example 2

Total amine (1°+2°+3°): $1000 \times 10^{-6}$ mol/g
Secondary plus tertiary amine (2°+3°): $1049 \times 10^{-6}$ mol/g
Tertiary amine (3°): $929 \times 10^{-6}$ mol/g The results show that 93% of the total amine present was of the tertiary form.

EXAMPLE 3

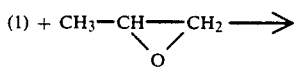

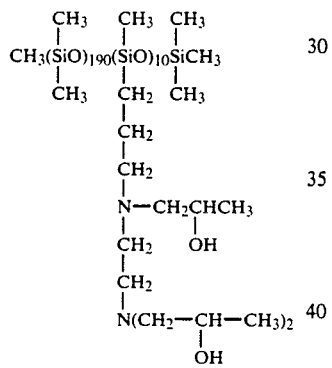

As in Example 2, 250 g of Amodimethicone Oil (1) and 33 g of propylene oxide were reacted initially at 50° C. and 100 psi until an exotherm of approximately 70° C. was observed. Following the exotherm, the reaction was carried out at 100° C. and 100 psi for about 20-24 hours. The product was "stripped" and analyzed as in Example 2.

Results of Titration —Example 3

Total amine: $1110 \times 10^{-6}$ mol/g
Secondary plus tertiary amine $1077 \times 10^{-6}$ mol/g
Tertiary amine: $947 \times 10.6$ mol/g Approximately 85% of Total amine was converted to tertiary form.

EXAMPLE 4

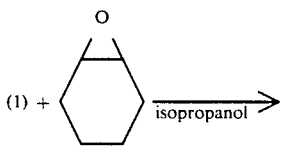

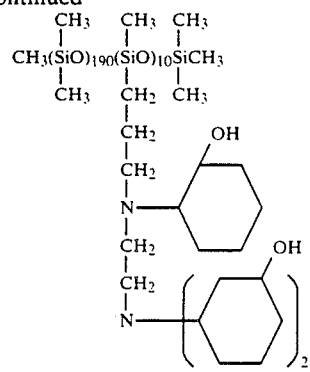

As in Example 2, 75 g of (1) and 13.9g of cyclohexene oxide (ex Aldrich) together with 90 g of isopropanol (solvent) were placed in the pressure reactor and reacted initially at 50° C. and 100 psi for about 1 hour during which time an exotherm to 63° C. was observed. The final conditions were set at 100° C. and 100 psi and the reaction allowed to run for 20-24 hours. The product was Placed in a rotary evaporator and the solvent and unreacted material (isopropanol) removed under vacuum and heating. Analysis of product (brown color) was conducted as in Example 2.

Results of Titration—Example 4

Total amine $1070 \times 10^{-6}$ mol/g
Secondary plus tertiary amine $1075 \times 10^{-6}$ mol/g
Tertiary amine $96 \times 10^{-6}$ mol/g About 9% of the total amine content was converted to the tertiary form.

EXAMPLE 5

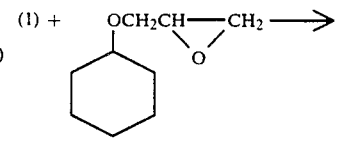

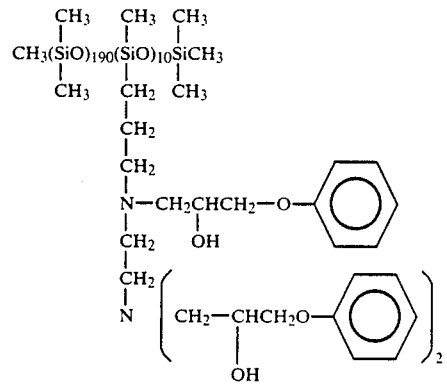

As in Example 4, 772 g of (1) and 22 g of 1,2 epoxy-3-phenoxy propane (ex Aldrich) and 95 g of 2-propanol were reacted together for 24 hours. The product was light brown in appearance. The amine content was determined as in Example 2.

Titration Results—Example 5

Total amine $530 \times 10^{-6}$ mol/g
Secondary plus tertiary amine $526 \times 10^{-6}$ mol/g Tertiary amine $446 \times 10^{-6}$ mol/g

Example 6

$$(1) + CH_3(CH_2)_{15}-CH\underset{O}{\overset{}{-\!\!\!-\!\!\!-}}CH_2 \longrightarrow$$

$$\begin{array}{c}
\phantom{xx}CH_3\phantom{xxx}CH_3\phantom{xx}CH_3\\
\phantom{xx}|\phantom{xxxxx}|\phantom{xxxx}|\\
CH_3(SiO)_{190}(SiO)_{10}SiCH_3\\
\phantom{xx}|\phantom{xxxxx}|\phantom{xxxx}|\\
\phantom{xx}CH_3\phantom{xxx}CH_2\phantom{xx}CH_3\\
\phantom{xxxxxxxx}|\\
\phantom{xxxxxxxx}CH_2\\
\phantom{xxxxxxxx}|\\
\phantom{xxxxxxxx}CH_2\\
\phantom{xxxxxxxx}|\\
\phantom{xxxxxx}N-CH_2-CH-(CH_2)_{15}CH_3\\
\phantom{xxxxxxxx}|\phantom{xxxxxx}|\\
\phantom{xxxxxxxx}CH_2\phantom{xxxx}OH\\
\phantom{xxxxxxxx}|\\
\phantom{xxxxxxxx}CH_2\\
\phantom{xxxxxxxx}|\\
\phantom{xxxxxxxx}N[CH_2-CH-(CH_2)_{15}-CH_3]_2\\
\phantom{xxxxxxxxxxxxxxx}|\\
\phantom{xxxxxxxxxxxxxxx}OH
\end{array}$$

As in Example 4, 65 g of (1), 33 g of 1,2-epoxy-octadecane (ex Aldrich) and 100 g of isopropanol were reacted together. The final product was a solid yellowish "wax" at room temperature which upon heating (45°–50° C.) becomes a viscous yellowish oil.

The product was analyzed as in Example 2 with one modification being made. It was necessary to use Toluene as a cosolvent together with acetic anhydride and glacial acetic acid since the product was found to be insoluble in a solution of acetic anhydride and glacial acetic acid alone.

Results of Titration—Example 6

Total amine $754 \times 10^{-6}$ mol/g
Secondary plus tertiary amine $673 \times 10^{-6}$ mol/g
Tertiary amine $611 \times 10^{-6}$ mol/g About 81% of the total amine content was converted to the tertiary form.

ALKYLATION OF AMINO FUNCTIONAL POLYDIMETHYLSILOXANE COPOLYMER

Example 7

(structure 2)

(structure 3)

where R = $(-CH_2)_3-NH-(CH_2)_2-NH_2$ $R^1 = (-CH_2)_3-N-(CH_2)_2-N(CH_2CH_2OH)_2$
          |
          $CH_2CH_2OH$ As in Example 2, 100 g of silicone fluid (2), 11.6 g of ethylene oxide and 110 g of 2-propanol were reacted together. The reaction conditions were 50° C. and 100 psi for 24 hours. The final stripped product was milky white in appearance. There were two changes made in the analysis of the product. First, chloroform was the solvent chosen for total as well as secondary plus tertiary amine determination since the product was insoluble in a solution of ether and isopropanol. Second, the hydrochloric acid titrant was 0.2N. The same phenomenon, observed in Example 1 where the titrating solution became turbid and formed a precipitate, was observed when titrating this product for total and secondary plus tertiary amine content. The titration showed that all amines were converted to tertiary amines.

ANTICARIES PROPERTY OF AMINOSILICONES AS DEMONSTRATED BY THE DISSOLUTION TEST OF HYDROXYAPATITE POWDER

EXAMPLE 8

In these sequential exposure experiments, hydroxyapatite powder (3.5%) was first treated with a 5% silicone emulsion (60–70ml) for ten minutes, filered, washed with distilled water, and then exposed in a pH 5, 150ml acetic acid solution including 5% silicone emulsion. Aliquots were withdrawn at various time intervals and filtered off the hydroxyapatite powder. The amounts of phosphate ion in the aliquots were measured by UV spectrophotometry at 710 nm with molybdate solution in accordance with Official Methods of Analysis, Association of Official Analytical Chemists, edited by Sidney Williams, Arlington, Va., p. 632 (1984). The results are shown in Table 1.

The ethoxylated aminoalkyl silicone had the structure of (4) in Example 2.

TABLE 1

| ACID DISSOLUTION TESTS OF HYDROXYAPATITE POWDER WHICH WAS TREATED WITH AMINOSILICONES | | | | | | | | |
|---|---|---|---|---|---|---|---|---|
| | | 5 Min. | 10 Min. | 20 Min. | 30 Min. | 40 Min. | 50 Min. | 60 Min. |
| Sequential exposure | Ethoxylated Aminoalkyl silicone | 316 | 350 | 370 | 381 | 357 | 386 | 366 |
| | Polydimethylsiloxane | 344 | 358 | 380 | 404 | 380 | 431 | 417 |
| | Untreated HAP | 373 | 432 | 425 | 447 | 444 | 440 | 438 |

This experiment demonstrates that after 60 minutes exposure to the acid solution, the untreated powder lost 438 ppm phosphate ions whereas the one treated with the modified amino alkyl silicone of the invention lost only 366 ppm phosphate ion.

It should be understood that the specific forms of the invention herein illustrated and described are intended

We claim:

1. An organosiloxane comprised of at least one unit of formula A:

$$-R^2{}_mN-(CH_2CH_2N)_n-R^1-SiO_{(3-a)/2}-$$
$$\phantom{-R^2{}_mN-(CH_2CH_2N)_n-}|\phantom{-R^1-}|$$
$$\phantom{-R^2{}_mN-(CH_2CH_2N)_n-}R^2{}_b\phantom{---}R_a$$
A wherein a is from 0 to 2, n is from 1 to 5, R is a monovalent radical, $R^1$ is a divalent hydrocarbon radical, $R^2$ is $$-CH_2-CH-R^3$$
$$\phantom{-CH_2-}|$$
$$\phantom{-CH_2-}OH$$

$R^3$ is selected from the group consisting of hydrogen and monovalent hydrocarbon radicals, m is 1 or 2, and b is 0 or 1.

2. Organosiloxane of claim 1 wherein said unit is $$(HOCH_2CH_2)_2NCH_2CH_2N-CH_2CH_2CH_2SiO-$$
$$\phantom{(HOCH_2CH_2)_2NCH_2CH_2N-}|\phantom{CH_2CH_2CH_2Si}|$$
$$\phantom{(HOCH_2CH_2)_2NCH_2CH_2N-}CH_2\phantom{CH_2CH_2Si}CH_3$$
$$\phantom{(HOCH_2CH_2)_2NCH_2CH_2N-}|$$
$$\phantom{(HOCH_2CH_2)_2NCH_2CH_2N-}CH_2$$
$$\phantom{(HOCH_2CH_2)_2NCH_2CH_2N-}|$$
$$\phantom{(HOCH_2CH_2)_2NCH_2CH_2N-}OH$$

3. The organosiloxane of claim 1 wherein n is 1.

4. The organosiloxane of claim 1 wherein R is selected from the group consisting of hydrocarbon radicals, halogenated hydrocarbon radicals, hydrogen, hydroxyl and alkoxyl.

5. The organosilicone of claim 1 wherein R is selected from the group consisting of methyl, phenyl and -trifluoropropyl.

6. The organosiloxane of claim 1 wherein $R^1$ comprises 3 or more carbons.

7. The organosiloxane of claim 1 where $R^3$ is selected from the group consisting of methyl and phenyl.

8. The organosiloxane of claim 1 further comprising at least one unit of formula B, $$R^5{}_aR^4{}_cSiO_{(4a-c)/2}$$
B wherein $R^4$ and $R^5$ are monovalent radicals which can be the same or different, a and c are integers of 0, 1, 2 or 3 and a plus c is 1, 2 or 3.

9. The organosiloxane of claim 8 wherein $R^4$ and $R^5$ are independently selected from the group consisting of hydrocarbon radicals, halogenated hydrocarbons, hydrogen and alkoxyls.

10. The organosiloxane of claim 9 wherein $R^4$ and $R^5$ are selected independently from the group consisting of methyl, phenyl and -trifluoropropyl.

11. The organosiloxane of claim 8 wherein a plus c equals 2.

12. The organosiloxane of claim 8 comprising a random copolymer of formulas A and B.

13. The organosiloxane of claim 8 comprising a block copolymer of formulas A and B.

14. The organosiloxane of claim 8 comprising a linear copolymer of formulas A and B.

15. The organosiloxane of claim 8 comprising a branched copolymer of formulas A and B.

16. The organosiloxane of claim 8 where units of formula A comprise from 0.5 to 100% by repeat unit.

17. The organosiloxane of claim 8 wherein units of formula A comprise from 1 to 10% by repeat unit.

18. The organosiloxane of claim 8 having a molecular weight of between 5,000 and 100,000.

19. The organosiloxane of claim 8 having the formula $$Me_3Si(Me_2SiO)_x(Me_2SiO)_ySiMe_3$$
$$|$$
$$CH_2$$
$$|$$
$$CH_2$$
$$|$$
$$CH_2$$
$$|$$
$$N-CH_2CH_2OH$$
$$|$$
$$CH_2$$
$$|$$
$$CH_2$$
$$|$$
$$N-CH_2CH_2OH$$
$$|$$
$$CH_2CH_2OH$$

wherein x and y are randomly arranged and x is from 750 to 1250 and y is from 25 to 100.

20. The organosiloxane of claim 8 having the formula $$Me_3Si(Me_2SiO)_x(MeSiO)_ySiMe_3$$
$$|$$
$$CH_2$$
$$|$$
$$CH_2$$
$$|$$
$$CH_2$$
$$|$$
$$N-CH_2CH_2OH$$
$$|$$
$$CH_2$$
$$|$$
$$CH_2$$
$$|$$
$$N-CH_2CH_2OH$$
$$|$$
$$CH_2CH_2OH$$

wherein the organosiloxane is a block copolymer and x is from 750 to 1250 and y is from 25 to 100.

21. The compound of claim 1 wherein n=1.

22. The organosiloxane of claim 1 wherein $R^3$ is a hydrocarbon radical including 10 or fewer carbon atoms.

23. The organosiloxane wherein $R^3$ is hydrogen.

* * * * *